(12) United States Patent
Wu et al.

(10) Patent No.: US 11,344,892 B2
(45) Date of Patent: May 31, 2022

(54) DIGITAL PCR SYSTEM AND A METHOD FOR FORMING DIGITAL PCR DROPLET

(71) Applicant: Shanghai Industrial μTechnology Research Institute, Shanghai (CN)

(72) Inventors: Xuanye Wu, Shanghai (CN); Yimin Guan, Shanghai (CN)

(73) Assignee: Shanghai Industrial μTechnology Research Institute, Shanghai (CN)

( * ) Notice: Subject to any disclaimer, the term of this patent is extended or adjusted under 35 U.S.C. 154(b) by 0 days.

(21) Appl. No.: 16/622,939

(22) PCT Filed: Nov. 22, 2018

(86) PCT No.: PCT/CN2018/116929
§ 371 (c)(1),
(2) Date: Dec. 16, 2019

(87) PCT Pub. No.: WO2020/034479
PCT Pub. Date: Feb. 20, 2020

(65) Prior Publication Data
US 2021/0402408 A1 Dec. 30, 2021

(30) Foreign Application Priority Data
Aug. 13, 2018 (CN) .......................... 201810916861.2

(51) Int. Cl.
*B01L 7/00* (2006.01)
*B01L 3/00* (2006.01)

(52) U.S. Cl.
CPC ............ *B01L 7/52* (2013.01); *B01L 3/502784* (2013.01); *B01L 2200/16* (2013.01); *B01L 2300/1822* (2013.01); *B01L 2300/1844* (2013.01)

(58) Field of Classification Search
CPC .. B01L 7/52; B01L 3/502784; B01L 2200/16; B01L 2300/1822; B01L 2300/1844
See application file for complete search history.

(56) References Cited

U.S. PATENT DOCUMENTS

2009/0023189 A1* 1/2009 Lau ..................... B01F 13/0059
435/91.2

* cited by examiner

*Primary Examiner* — Christopher Adam Hixson

(57) ABSTRACT

The present disclosure provides a digital PCR system. The system includes a droplet formation assembly and a droplet orifice assembly. The droplet formation assembly includes a heat conducting plate and a cover plate, at least one inverted U-shaped step is placed on a side surface of the cover plate, the heat conducting plate, the cover plate and the inverted U-shaped step together form a droplet formation chamber having an opening at a bottom. The droplet orifice assembly is connected below the droplet formation assembly, and includes a plurality of droplet orifices, the droplet orifice is connected with the droplet formation chamber, and a vaporization component is placed in the droplet orifice, the vaporization component vaporizes a digital PCR solution in the droplet orifice and rapidly pushes the digital PCR solution into a droplet forming oil in the droplet formation chamber, to form a digital PCR droplet.

37 Claims, 13 Drawing Sheets

DIGITAL PCR SYSTEM AND A METHOD FOR FORMING DIGITAL PCR DROPLET

CROSS REFERENCE TO RELATED APPLICATION

This is a Sect. 371 National Stage of PCT International Application No. PCT/CN2018/116929, filed on 22 Nov. 2018, which claims priority of a Chinese Patent Application No. 2018109168612 filed on 13 Aug. 2018, the contents of both applications hereby being incorporated by reference in their entireties for all purposes.

BACKGROUND

Field of Disclosure

The present disclosure relates to the field of biomedicine, in particular, to the field of disease detection, and more particularly, to an integrated in-situ digital PCR system and a method for forming droplet.

Description of Related Arts

Polymerase Chain Reaction (PCR) has been proposed for 20 years, during this time, PCR has developed into a key and conventional technology in the field of molecular biology, which has greatly promoted the development of various fields of the life science. Especially in the late 1990s, real time PCR (qPCR) technology and related products launched by American ABI Company developed PCR from in vitro synthesis and qualitative/semi-quantitative detection technology into a highly sensitive, highly specific and accurate quantitative genetic analysis technique.

After rapid development over a decade, qPCR technology has been used to diagnose diseases except for trauma and nutritional deficiencies. However, there are many factors that affect the amplification efficiency during PCR amplification process. It is not guaranteed that the amplification efficiency remains the same during the reaction process, and that the amplification efficiencies of the actual sample, the standard sample and different samples are the same. The cycle threshold (CT), on which the quantitative analysis relies, therefore is not constant. Therefore, the quantification of qPCR is only "relative quantification", the accuracy and reproducibility of qPCR cannot meet the requirements of quantitative analysis of molecular biology.

At the end of the 20th century, Vogelstein et al. proposed the concept of digital PCR (dPCR). A sample is divided into tens to tens of thousands of parts, then assigned to different reaction units, each unit contains one or more copies of a target molecule (DNA template). The target molecules were separately subjected to PCR amplification in each reaction unit, and fluorescence signals of each reaction unit were statistically analyzed after the amplification is completed. Unlike qPCR, digital PCR does not depend on CT values, therefore, digital PCR is not affected by amplification efficiency. After the amplification is completed, the average concentration (content) of each reaction unit is calculated by direct counting or Poisson distribution formula, the error can be controlled within 5%. Digital PCR can achieve absolute quantitative analysis without comparing with the standard sample and standard curve.

Digital PCR (also known as single molecule PCR) generally consists of two parts, PCR amplification and fluorescence signal analysis. In the PCR amplification phase, unlike conventional techniques, digital PCR generally requires diluting the sample to a single molecule level, and distributing diluted sample evenly to tens to tens of thousands of units to react. Unlike the method in which qPCR performs real time fluorescence measurement on each cycle, the digital PCR technique collects the fluorescence signal of each reaction unit after the amplification is completed. Finally, the original concentration or content of the sample is calculated by direct counting or Poisson distribution formula.

Digital PCR is an absolute quantitative technique for nucleic acid molecules. The number of DNA molecules can be directly counted. Digital PCR is an absolute quantification of the original sample, so it is especially suitable for applications that cannot be distinguished by CT values. For example, copy number variation, mutation detection, gene relative expression studies (such as allelic imbalance expression), second generation sequencing results verification, miRNA expression analysis, single-cell gene expression analysis, and the like.

Three main types of digital PCR technology are currently available on the market. In one PCR technology, droplets are formed by cutting the PCR solution of aqueous phase using a flowing oil in a specific instrument, and then PCR and detection are performed in two other instruments. In another PCR technology, the PCR solution is distributed onto a hollowed-out silicon wafer, then PCR is performed in a specific instrument and detection is performed in another instrument. In the last PCR technology, a liquid is injected through a narrow channel into a cavity on an instrument to form a droplet, and PCR is performed, then detection is performed in another instrument. However, the droplet formation speeds or fluxes of the current three methods are respectively limited. In addition, the above three technologies rely on multiple large instruments without exception. This not only increases the cost of instrument purchase, but also limits the widespread use of digital PCR. It also increases the complexity of the experimental operation.

Therefore, how to provide a high-speed digital PCR droplet formation technology that forms more than 1000 droplets per second, an in-situ PCR technology for droplet formation and PCR temperature control and detection instrument integration, and an efficient digital PCR oil utilization method, has become an important technical problem to be solved by those skilled in the art.

SUMMARY OF THE PRESENT DISCLOSURE

The present disclosure provides an integrated in-situ digital PCR system and a method for forming droplet, to solve the problem of slow droplet formation, small flux, complicated operation, low utilization of PCR oil in traditional technology.

The present disclosure provides a digital PCR system, including: a droplet formation assembly and a droplet orifice assembly.

The droplet formation assembly includes a heat conducting plate and a cover plate, at least one inverted U-shaped step is placed on a side surface of the cover plate, the heat conducting plate, the cover plate and the inverted U-shaped step together form a droplet formation chamber having an opening at a bottom.

The droplet orifice assembly is connected below the droplet formation assembly and includes a plurality of droplet orifices. The droplet orifice is opened from a top surface of the droplet orifice assembly, and extends toward a bottom surface of the droplet orifice assembly, but does not penetrate the lower surface of the droplet orifice assembly, the droplet orifice is connected with the droplet formation chamber, and a vaporization component is placed in the droplet orifice, the vaporization component vaporizes a digital PCR solution in the droplet orifice and rapidly pushes the digital PCR solution into a droplet forming oil in the droplet formation chamber, to form a digital PCR droplet.

Optionally, the droplet orifice assembly includes a thermal bubble print chip.

Optionally, a height of the inverted U-shaped step is less than twice a diameter of the digital PCR droplet to be formed, such that the digital PCR droplet is tiled in the droplet formation chamber.

Optionally, a side surface of the heat conducting plate facing the cover plate contains a boss placed along an outer edge of the inverted U-shaped step.

Optionally, a part of the heat conductive plate close to the opening of the droplet formation chamber gradually extends outward to form a slope, so as to expand a size of the opening of the droplet formation chamber.

Optionally, the droplet formation assembly further includes at least one droplet formation oil injection hole, the droplet formation oil injection hole penetrates the heat conducting plate and is connected with the droplet formation chamber.

Optionally, the droplet formation assembly further includes at least one droplet formation chamber vent, the droplet formation chamber vent penetrates the heat conducting plate and is connected with the droplet formation chamber.

Optionally, the vaporization component is placed on a bottom surface or a side wall of the droplet orifice.

Optionally, a shape of the opening of the droplet orifice comprises any one of a circle, an ellipse, and a polygon.

Optionally, the vaporization component includes a heating component that vaporizes the liquid layer of the digital PCR solution by heating. Optionally, the heating component includes at least one metal layer.

Optionally, the PCR system further includes at least one PCR reagent chamber storing a digital PCR solution, a flow channel is placed in the droplet orifice assembly, the droplet orifice is connected with the PCR reagent chamber through the flow channel.

Optionally, the flow channel includes at least one main flow channel and a plurality of branch flow channels connected with the main flow channel, and each of the droplet orifices is respectively connected with one of the branch flow channels.

Optionally, the digital PCR system further includes a pedestal, the PCR reagent chamber contains an opening, the opening extends from a top surface of the pedestal toward a bottom surface of the pedestal but does not penetrate the bottom surface of the pedestal, the droplet orifice assembly is coupled with the top surface of the pedestal and covers the opening of the PCR reagent chamber.

Optionally, at least one digital PCR solution injection hole is placed on the bottom surface of the pedestal, and the digital PCR solution injection hole is connected with the PCR reagent chamber.

Optionally, at least one PCR reagent chamber vent is placed on the bottom surface of the pedestal, the PCR reagent chamber vent is connected with the PCR reagent chamber.

Optionally, the digital PCR system further includes a flexible circuit board, the flexible circuit board is connected above the pedestal, a through hole is placed in the flexible circuit board to accommodate the droplet orifice assembly, a plurality of first connection pads and a plurality of second connection pads are placed on a surface of the flexible circuit board, and the droplet orifice assembly is connected with the first connection pad by a wire.

Optionally, the flexible circuit board is adhesively attached to the pedestal.

Optionally, at least one channel is placed on the surface of the pedestal to prevent glue from flowing onto the droplet orifice assembly, the channel is distributed over the outer circumference of the droplet orifice assembly.

Optionally, at least two positioning perforations are placed in the flexible circuit board, a positioning protrusion corresponding to a position of the positioning perforation is placed on the surface of the pedestal.

Optionally, the digital PCR system further includes a controller, the controller includes a controller housing and a controller circuit board located in the controller housing, the controller housing contains a supporting portion to place the pedestal, a plurality of circuit connecting conductive pins connected with the controller circuit board is placed on a surface of the supporting portion, and a position of the circuit connecting conductive pin corresponds to a position of the second connection pad.

Optionally, at least one limiting slot is placed at one end of the pedestal, and at least one limiting member corresponding to the limiting slot is placed at the controller housing.

Optionally, a limiting through hole is placed at the pedestal, the limiting through hole penetrates a front surface and a back surface of the pedestal, and a limiting member corresponding to the limiting through hole is placed at the controller housing.

Optionally, the controller further includes a cover, the cover is coupled with the controller housing to cover the pedestal.

Optionally, the digital PCR system further includes: an external semiconductor cooler to heat or cool the droplet formation chamber.

Optionally, the external semiconductor cooler contains a fan.

Optionally, the digital PCR system further includes: an external temperature sensor to test a temperature of the droplet formation chamber.

Optionally, the digital PCR system further includes: an optical detection system performing PCR signal collection detection without transferring a sample.

Optionally, a material of the cover plate is transparent.

The present disclosure further provides a method for forming digital PCR droplet, including: injecting a digital PCR solution into a PCR reagent chamber, the digital PCR solution enters a droplet orifice connecting with the PCR reagent chamber to form a liquid layer; adding a droplet formation oil to a droplet formation chamber, wherein the droplet formation chamber is formed by a heat conducting plate, a cover plate, and an inverted U-shaped step placed on one side surface of the cover plate; vaporizing the digital PCR solution through a vaporization component, and rapidly pushing the digital PCR solution into the droplet formation oil in the droplet formation chamber, to form the digital PCR droplet.

Optionally, the vaporization component includes a heating component that vaporizes the liquid layer by heating.

Optionally, a formation speed of the digital PCR droplet is controlled by controlling a heating time, a number of heating times, and a heating interval time of the heating component.

Optionally, a thickness of the liquid layer ranges from 0.2 nm to 30,000 nm.

Optionally, a thickness of the droplet formation chamber is less than twice a diameter of the digital PCR droplet to be formed, such that the resulting digital PCR droplet is tiled in the droplet formation chamber.

Optionally, after the digital PCR solution in the PCR reagent chamber is completely pushed into the droplet formation chamber to form the digital PCR droplet, the PCR reagent chamber is filled with the droplet formation oil.

Optionally, the droplet formation chamber is heated or cooled by an external semiconductor cooler.

Optionally, the digital PCR droplet is formed at a rate greater than 1000 droplets per second.

As described above, the digital PCR system and the method for forming the digital PCR droplet of the present disclosure have the following beneficial effects:

(1) The present disclosure uses a thermal bubble technique to perform high-speed digital PCR droplet formation. The rapid droplet formation depends on the instantaneous heating and vaporization of the nano-thickness liquid layer by the vaporization component in the droplet orifice, thereby rapidly pushing the digital PCR solution in the droplet orifice into the droplet formation oil, to form digital PCR droplets. The droplet formation technique of the present disclosure can achieve a droplet formation speed of greater than 1000 droplets per second, while the formation speed of the product on the market is 100 droplets per second.

(2) Compared with the method in which the oil phase and the water phase move together to produce droplets, the oil phase in the technical solution of the present disclosure is static, so the consumption of the oil phase is greatly reduced, and the amount of oil phase is reduced by about 50%.

(3) In-situ temperature-controlled PCR can be achieved by using an external semiconductor cooler to accurately control the temperature of the droplet formation chamber. The integrated optical system can be tested without transferring the sample. This reduces the operating time and improves the accuracy of the detection by reducing human errors.

(4) The in-situ digital PCR droplets can be tiled.

DESCRIPTION OF REFERENCE NUMERALS

Figure 1:
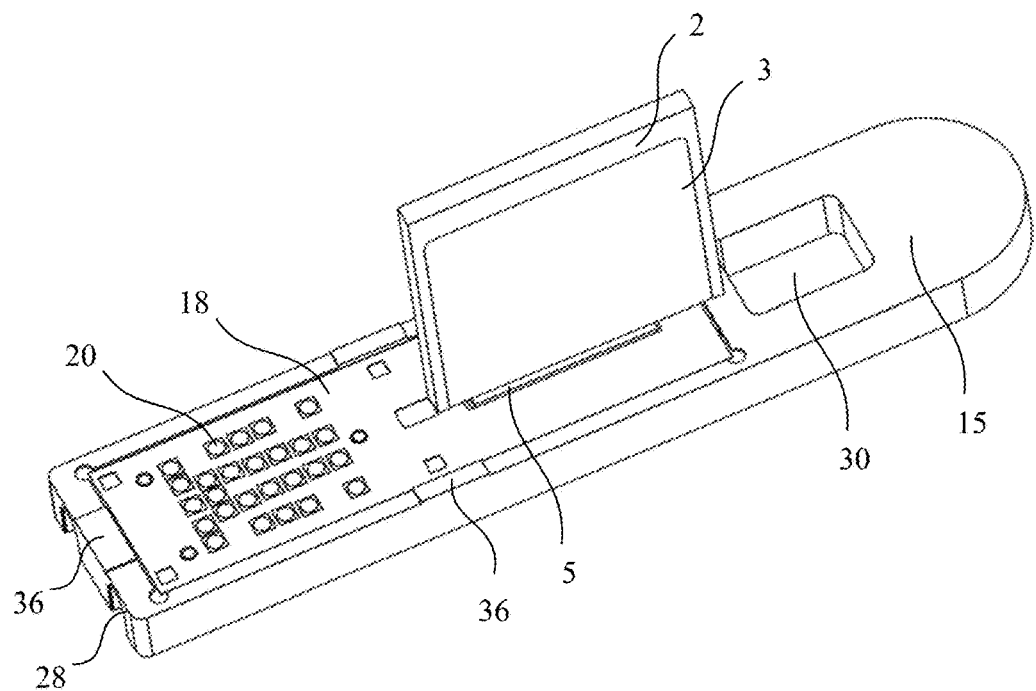
FIG. 1 shows a schematic perspective view of a digital PCR system of the present disclosure.

1 Droplet formation assembly
2 Heat conducting plate
3 Cover plate
4 Inverted U-shaped step
5 Droplet orifice assembly
6 Droplet orifice
7 Vaporization component
8 Boss
9 Slope
10 Droplet formation oil injection hole
11 Droplet formation chamber vent
12 PCR reagent chamber
13 Main flow channel
14 Branch flow channel
15 Pedestal
16 Digital PCR solution injection hole
17 PCR reagent chamber vent
18 Flexible circuit board
19 Through hole
20 Second connection pad 21 Channel
22 Positioning perforation
23 Positioning protrusion
24 Controller
25 Controller housing
26 Supporting portion
27 Circuit connection conductive pin
28 Limiting slot
29, 31 Limiting member
30 Limiting through hole
32 Cover
33 External semiconductor cooler
34 Fan
35 Sunken platform
36 Protrusion
37 Circuit board connection point
38 Housing support structure
39 Vent

DETAILED DESCRIPTION OF THE
PREFERRED EMBODIMENTS

The embodiments of the present disclosure will be described below. Those skilled in the art can easily understand other advantages and effects of the present disclosure according to contents disclosed by the specification. The present disclosure can also be implemented or applied through other different specific embodiments. Various modifications or changes can also be made to all details in the specification based on different points of view and applications without departing from the spirit of the present disclosure.

Referring to FIGS. 1-39. It needs to be stated that the drawings provided in the following embodiments are just used for schematically describing the basic concept of the present disclosure, thus only illustrating components only related to the present disclosure and are not drawn according to the numbers, shapes and sizes of components during actual implementation, the configuration, number and scale of each component during actual implementation thereof may be freely changed, and the component layout configuration thereof may be more complex.

Embodiment 1

Figure 2:
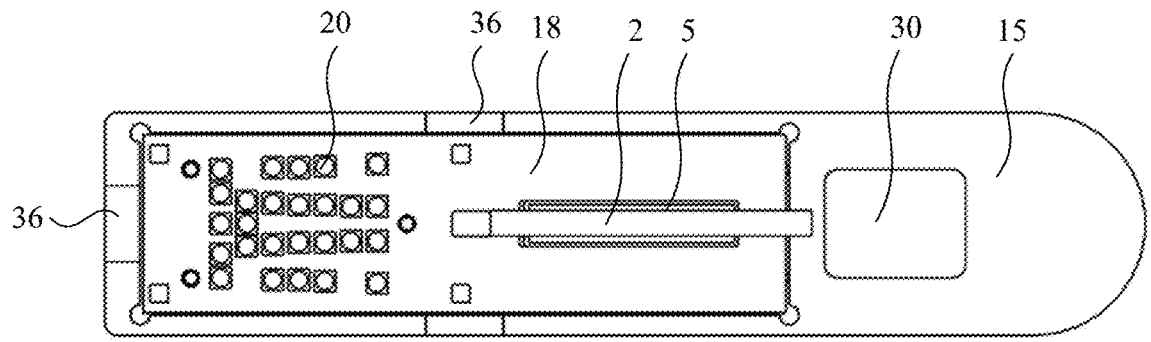
FIG. 2 shows a top view of the digital PCR system of the present disclosure.
Figure 3:
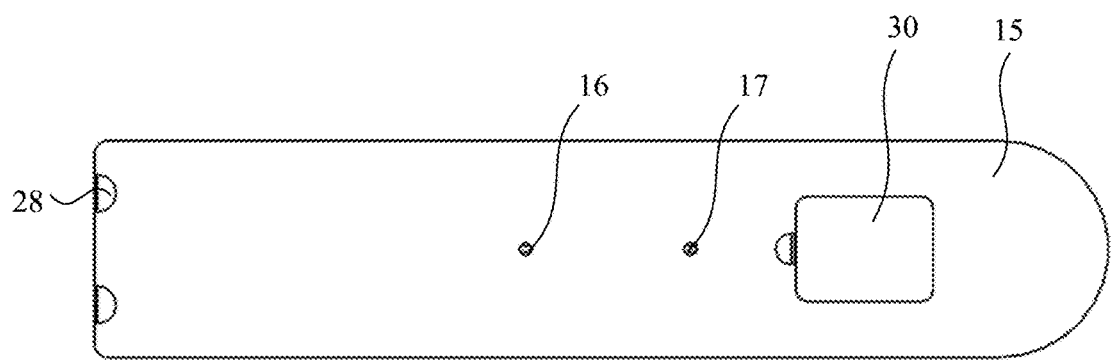
FIG. 3 shows a bottom view of the digital PCR system of the present disclosure.
Figure 4:
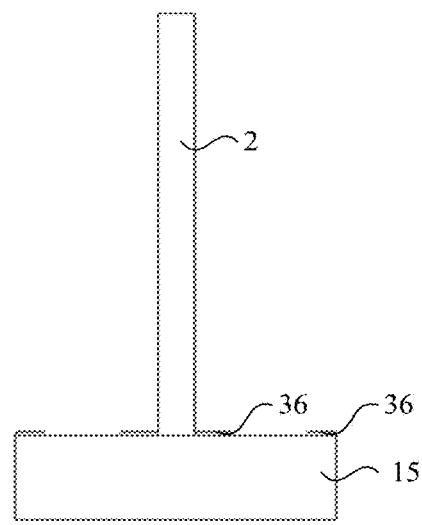
FIGS. 4-7 show side views of the digital PCR system of the present disclosure.
Figure 5:
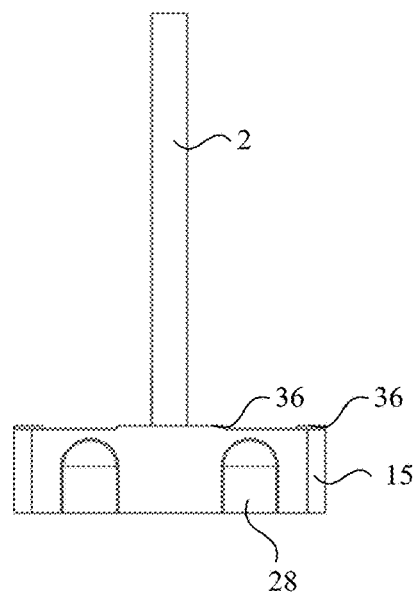
Figure 6:
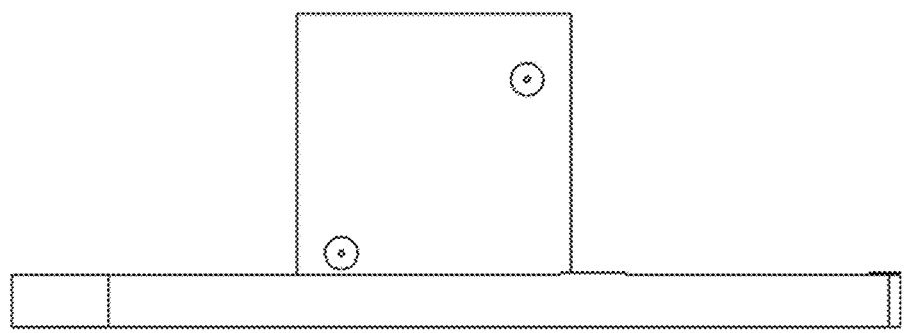
Figure 7:
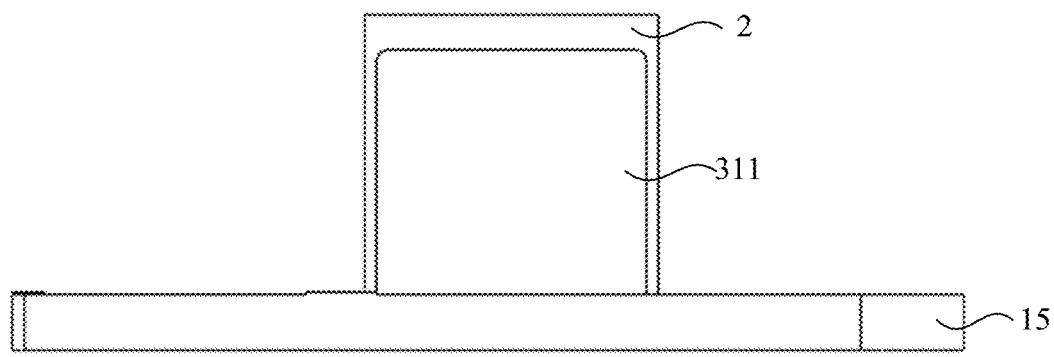

The present disclosure provides a digital PCR system. Referring to FIGS. 1-7. FIG. 1 shows a schematic perspective view showing the digital PCR system. FIG. 2 shows a top view of the digital PCR system, and FIG. 3 shows a bottom view of the digital PCR system, FIGS. 4, 5, 6, and 7 show side views of the digital PCR system in four directions.

Figure 8:
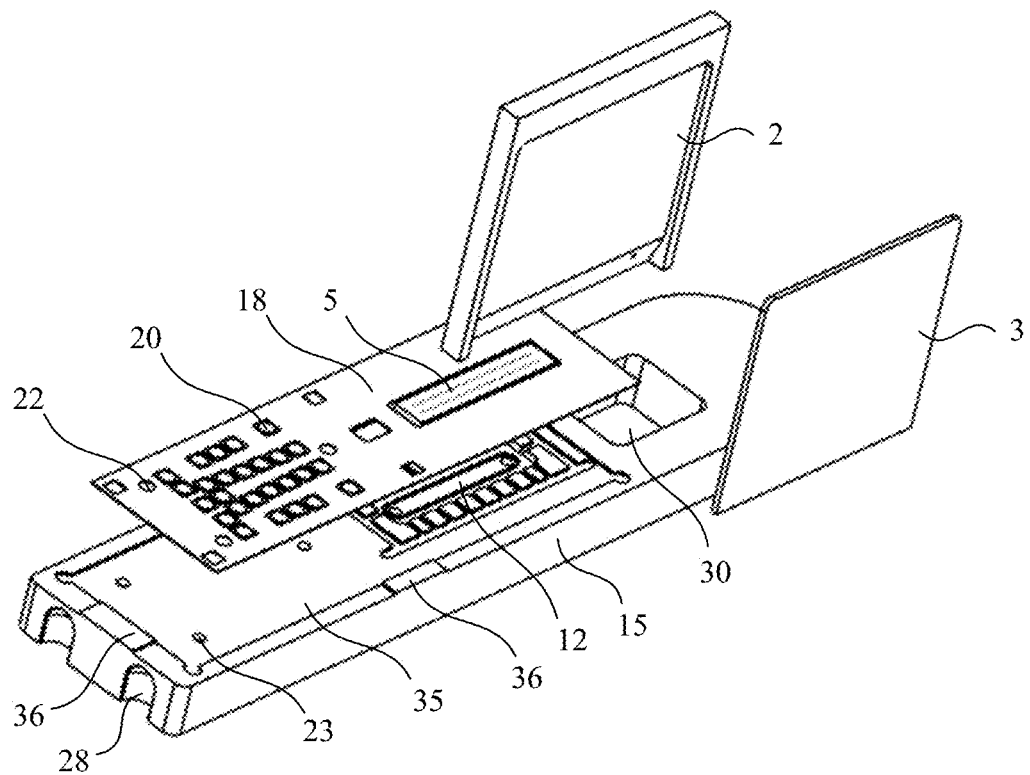
FIG. 8 is an exploded schematic diagram showing the digital PCR system of the present disclosure.

Referring to FIG. 8, which shows an exploded diagram of the digital PCR system, the digital PCR system includes a droplet formation assembly 1 and a droplet orifice assembly 5, the droplet orifice assembly 5 is connected below the droplet formation assembly 1.

Figure 9:
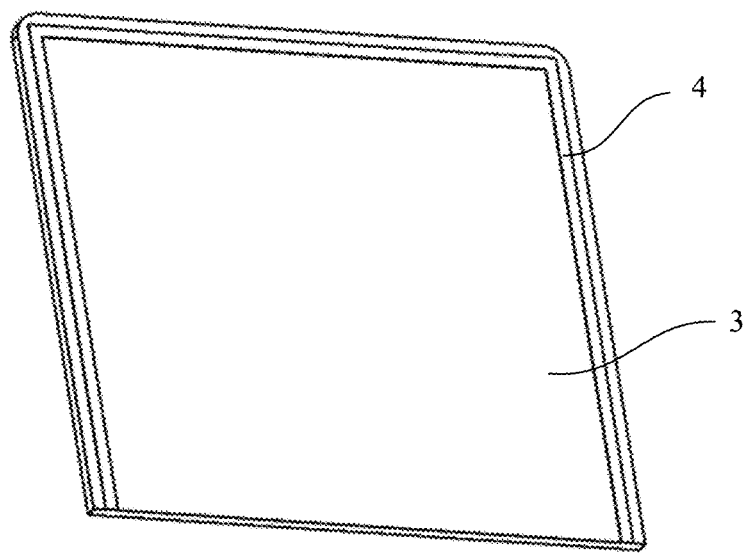
FIG. 9 shows a schematic perspective view of the cover plate of the digital PCR system of the present disclosure.
Figure 10:
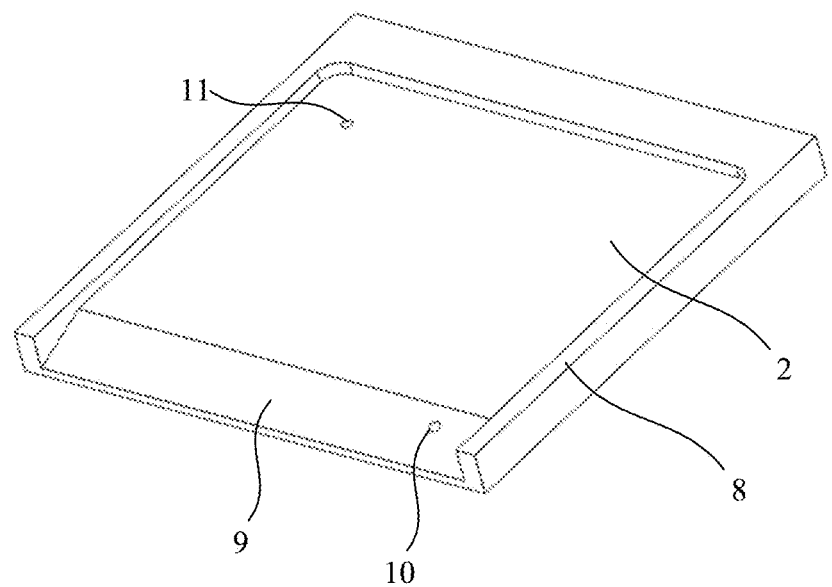
FIG. 10 shows a schematic perspective view of a heat conducting plate in the digital PCR system of the present disclosure.
Figure 11:
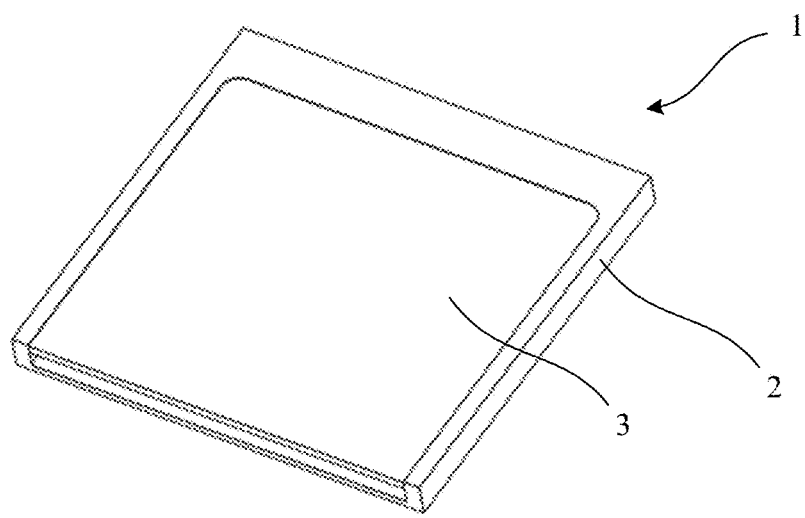
FIG. 11 shows a schematic perspective view of a droplet formation assembly in the digital PCR system of the present disclosure.

Specifically, the droplet formation assembly 1 includes a heat conducting plate 2 and a cover plate 3. Referring to FIGS. 9-10, FIG. 9 is shows schematic perspective view of the cover plate 3, and FIG. 10 shows a schematic perspective view of the heat conducting plate 2. As shown in FIG. 9, at least one inverted U-shaped step 4 is placed on a side surface of the cover plate 3.

Figure 12:
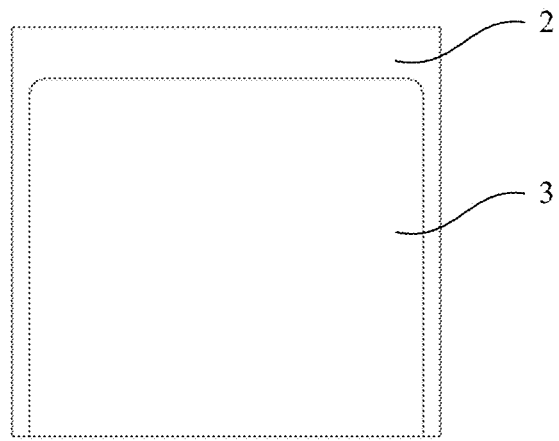
FIG. 12 shows a top view of a droplet formation assembly in the digital PCR system of the present disclosure.
Figure 13:
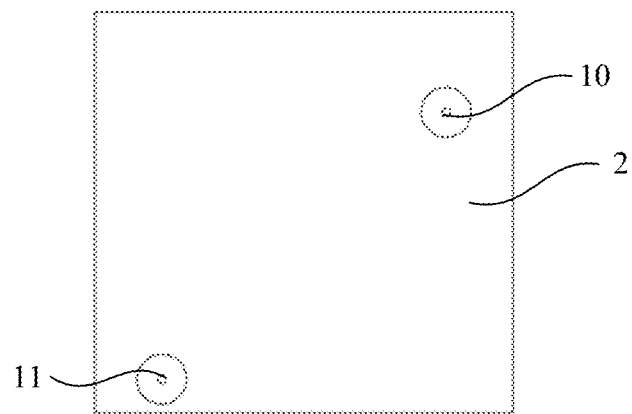
FIG. 13 shows a bottom view of a droplet formation assembly in the digital PCR system of the present disclosure.
Figure 14:
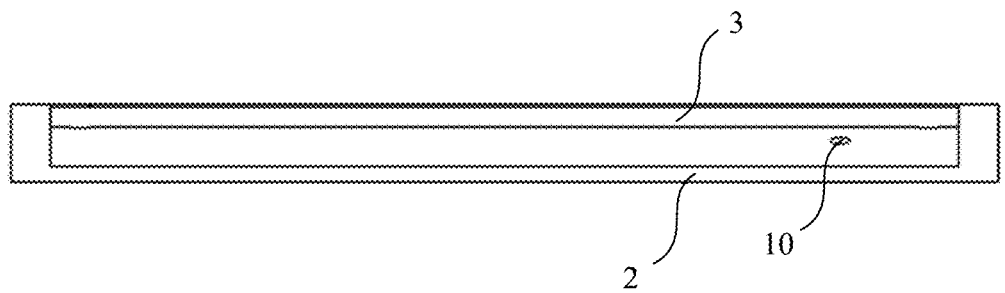
FIGS. 14-17 show side views of a droplet formation assembly in the digital PCR system of the present disclosure.
Figure 15:
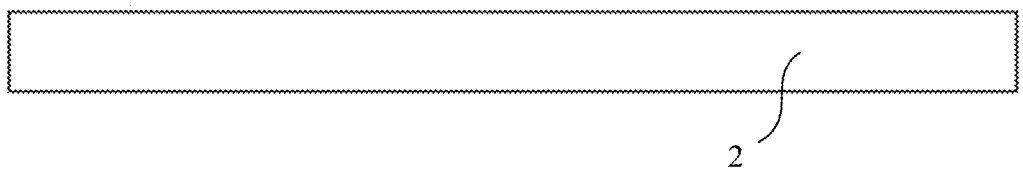
Figure 16:
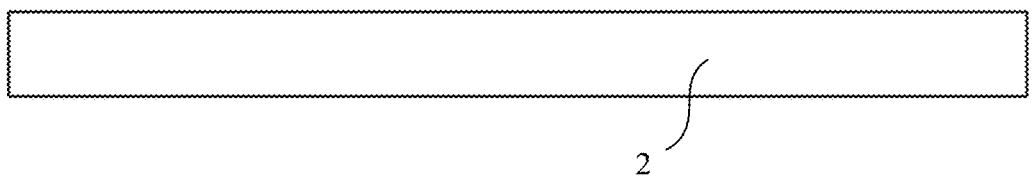
Figure 17:
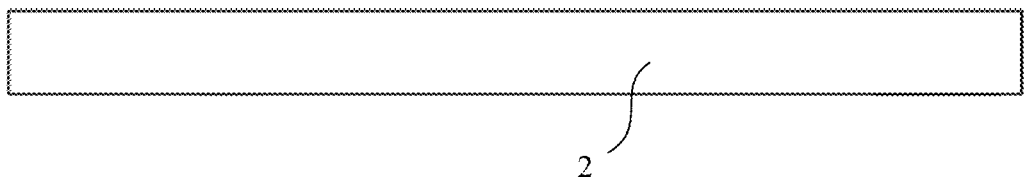

Referring to FIGS. 11-17, FIG. 11 shows a schematic perspective view the of the droplet formation assembly 1 combined by the heat conducting plate 2 and the cover plate 3. FIG. 12 shows a top view of the droplet formation assembly 1. FIG. 13 shows a bottom view of the droplet formation assembly 1. FIGS. 14, 15, 16, and 17 show side views of the droplet formation assembly 1 in four directions. The heat conducting plate 2, the cover plate 3 and the inverted U-shaped step 4 together form a droplet formation chamber. The droplet formation chamber has an opening at a bottom. In this embodiment, the number of the inverted U-shaped steps 4 is one, and correspondingly, the number of the droplet formation chambers is also one. In other embodiments, the number of the inverted U-shaped steps 4 may be more than one, to construct a plurality of droplet formation chambers.

Specifically, a height of the inverted U-shaped step 4 is less than twice a diameter of the digital PCR droplet to be formed, such that the resulting digital PCR droplet is tiled in the droplet formation chamber.

As an example, as shown in FIG. 9, the inverted U-shaped step 4 is formed by connecting three straight-line steps. In other embodiments, the inverted U-shaped step 4 may not be limited to a straight line. For example, the inverted U-shaped step 4 may be composed of a straight step and a curved step. The protection scope of the present disclosure should not be unduly limited herein.

As an example, the inverted U-shaped step 4 may be obtained by photoetching or etching the cover plate 3. The inverted U-shaped step 4 may be a double-sided tape of suitable thickness. There is a predetermined distance between the inverted U-shaped step 4 and an outer edge of the cover plate 3. If the cover plate 3 and the heat conducting plate 2 are glued, the peripheral area of the inverted U-shaped step 4 may be used to dispense glue.

Specifically, the material of the cover plate 3 includes, but is not limited to, one of transparent or opaque plastic and glass. The cover plate 3 may be made of metal. In this embodiment, the cover plate 3 is preferably made of a transparent material.

As an example, as shown in FIG. 10, a side surface of the heat conducting plate 2 facing the cover plate 3 contains a boss 8 placed along an outer edge of the inverted U-shaped step 4. The boss 8 serves to position the bonding of the cover plate 3. In this embodiment, the height of the boss 8 is equivalent to the thickness of the cover plate 3. Of course, the absolute height of the boss 8 is not important and can be adjusted as needed.

As an example, as shown in FIG. 10, a part of the heat conductive plate 2 close to the opening of the droplet formation chamber gradually extends outward to form a slope 9, to expand a size of the opening of the droplet formation chamber. The slope 9 can reserve a space for the ejected droplets, to prevent the droplets ejected at a high speed from colliding with the formed droplets.

As an example, as shown in FIG. 10, the droplet formation assembly further includes at least one droplet formation oil injection hole 10, the droplet formation oil injection hole 10 penetrates the heat conducting plate 2, and is connected with the droplet formation chamber. In the present embodiment, the droplet formation oil injection hole 10 is preferably placed at the slope 9.

As an example, as shown in FIG. 10, the droplet formation assembly further includes at least one droplet formation chamber vent 11, the droplet formation chamber vent 11 penetrates the heat conducting plate 2 and is connected with the droplet formation chamber.

As an example, the droplet orifice assembly 5 may include a thermal bubble print chip. Thermal bubble printing technology is a major technology in the field of printers. The basic principle is to eject ink droplets by heating. In the present disclosure, the droplet orifice assembly 5 may use a traditional thermal bubble print chip.

Figure 18:
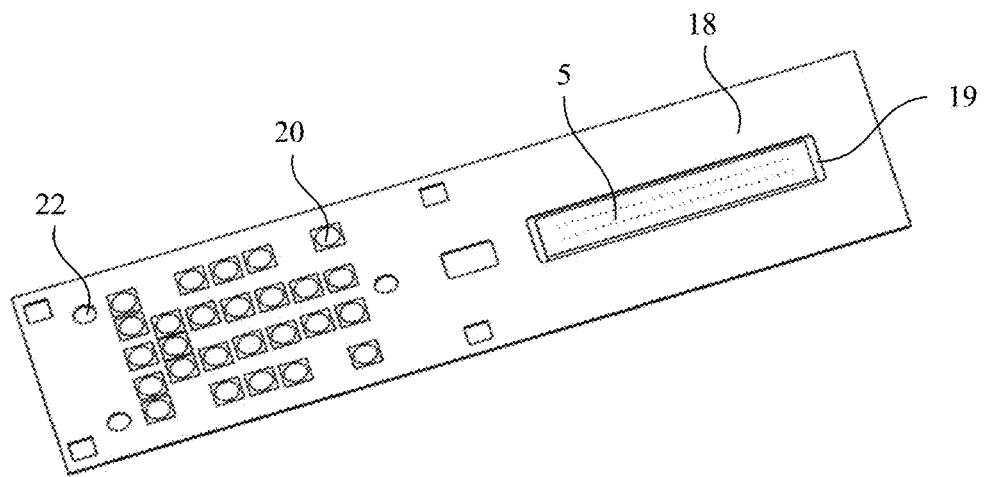
FIG. 18 shows a front perspective view showing the combination of a droplet orifice assembly and a flexible circuit board in the digital PCR system of the present disclosure.
Figure 19:
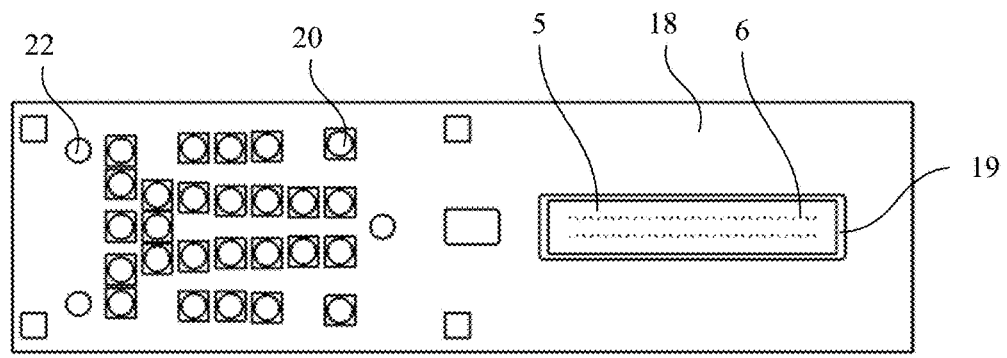
FIG. 19 shows a top view showing the combination of the droplet orifice assembly and the flexible circuit board in the digital PCR system of the present disclosure.
Figure 20:
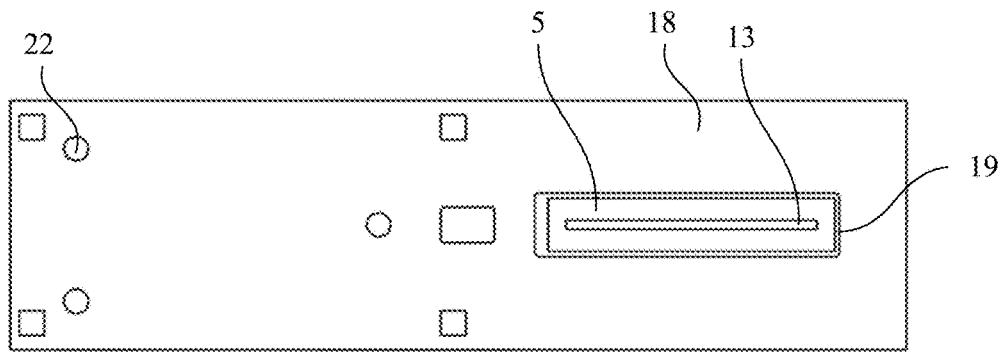
FIG. 20 shows a bottom view showing the combination of the droplet orifice assembly and the flexible circuit board in the digital PCR system of the present disclosure.
Figure 21:
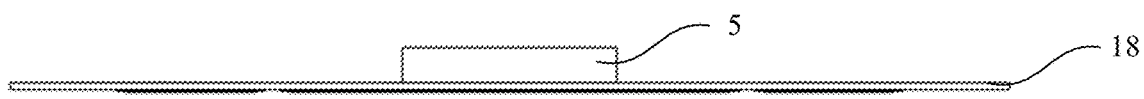
FIGS. 21-24 show side views showing the combination of a droplet orifice assembly and a flexible circuit board in the digital PCR system of the present disclosure.
Figure 22:
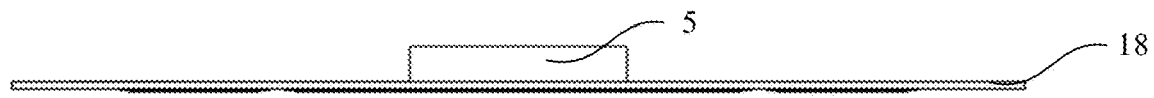
Figure 23:
Figure 24:

In this embodiment, the droplet orifice assembly 5 is connected with a flexible circuit board 18. Referring to FIGS. 18-24. FIG. 18 is a front view showing the combination of the droplet orifice assembly 5 and the flexible circuit board 18. FIG. 19 shows a top view of the combination of the droplet orifice assembly 5 and the flexible circuit board 18. FIG. 20 is a bottom view of the combination of the droplet orifice assembly 5 and the flexible circuit board 18. FIGS. 21, 22, 23, and 24 show side views of the combination of the droplet orifice assembly 5 and the flexible circuit board 18 in four directions.

Specifically, a through hole 19 is placed in the flexible circuit board 18 to accommodate the droplet orifice assembly 5. A plurality of first connection pads(not shown) and a plurality of second connection pads 20 are placed on a surface of the flexible circuit board 18. The droplet orifice assembly 5 is connected with the first connection pad by a wire. The droplet orifice assembly 5 is connected with an external controller via the flexible circuit board 18. The droplet orifice assembly 5 may be connected with the first connection pad by a standard WireBond process.

Figure 25:
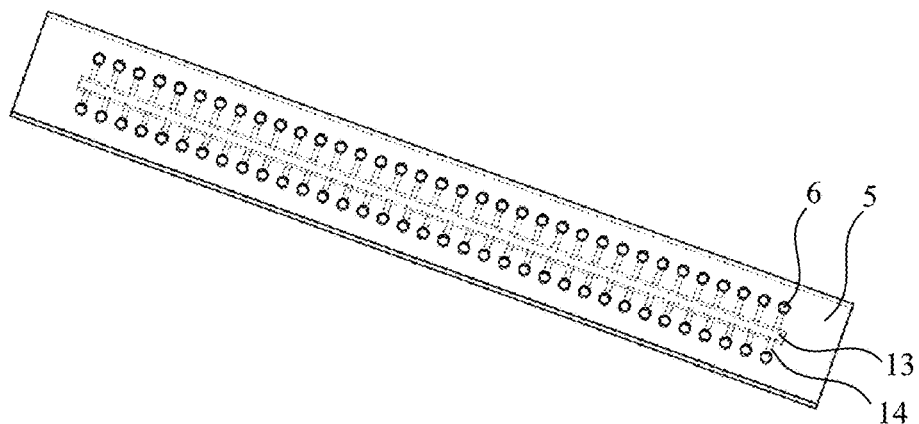
FIG. 25 shows a schematic perspective view of a droplet orifice assembly in the digital PCR system of the present disclosure.
Figure 26:
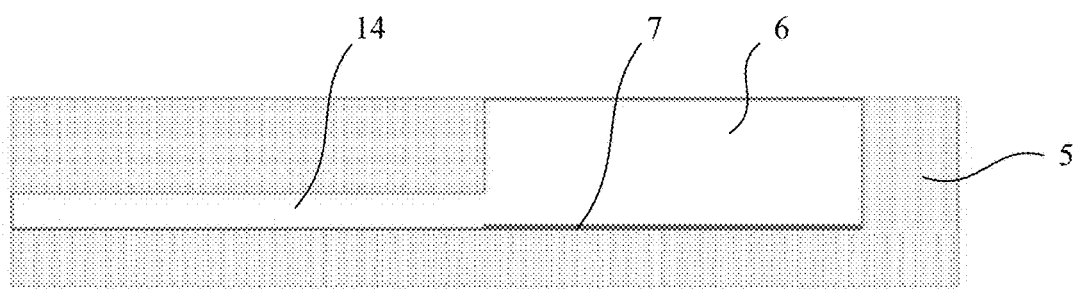
FIG. 26 shows a partial cross-sectional view of a droplet orifice assembly in the digital PCR system of the present disclosure.

Referring to FIGS. 25-26. FIG. 25 is a schematic perspective view showing the droplet orifice assembly 5, and FIG. 26 shows a partial cross-sectional view of the droplet orifice assembly 5. As shown in FIG. 25, the droplet orifice assembly 5 includes a plurality of droplet orifices 6, which are connected with the droplet formation chamber. In this embodiment, the droplet orifices 6 are arranged in two rows, and the droplet orifices in each row are uniformly distributed. In other embodiments, the droplet orifices 6 may be arranged in other ways, and the protection scope of the present disclosure should not be unduly limited herein. As shown in FIG. 26, the droplet orifice 6 is opened from the top surface of the droplet orifice assembly 5, and extends toward the lower surface of the droplet orifice assembly 5, but does not penetrate the bottom surface of the droplet orifice assembly 5. As an example, the shape of the opening of the droplet orifice 5 includes, but is not limited to, any one of a circle, an ellipse, and a polygon.

Specifically, as shown in FIG. 26, a vaporization component 7 is placed in the droplet orifice 6, to vaporize a liquid layer of a digital PCR solution in the droplet orifice 6 and rapidly push it into a droplet forming oil in the droplet formation chamber, to form a digital PCR droplet. The volume of the droplet orifice 6 determines the volume of the digital PCR droplet to be formed.

As an example, the vaporization component 7 is placed on the bottom surface of the droplet orifice 6. The vaporization component 7 may use a heating component that vaporizes the liquid layer of the digital PCR solution by heating. In this embodiment, the heating component includes a heating sheet, and the heating sheet may be a single metal layer or a composite multilayer metal layer. The shape of the vaporization component 7 includes, but is not limited to, a circle or a square, and the area of the vaporization component 7 may be 0.5 to 2 times the bottom area of the droplet orifice 6. In other embodiments, the vaporization component 7 may be placed on the sidewall of the droplet orifice 6. The protection scope of the present disclosure should not be unduly limited herein.

As shown in FIG. 8, the PCR system further comprises at least one PCR reagent chamber 12 to store the digital PCR solution. As shown in FIG. 25, a flow channel is placed in the droplet orifice assembly 5, the droplet orifice 6 is connected with the PCR reagent chamber 12 through the flow channel.

As an example, the flow channel includes at least one main flow channel 13 and a plurality of branch flow channels 14 connected with the main flow channel 13. Each of the droplet orifices 6 is respectively connected with one of the branch flow channels 14. FIGS. 20 and 25 show the case that the droplet orifice assembly 5 includes one main flow channel 13. In other embodiments, when the number of the droplet formation chambers is multiple, the number of the main flow channel 13 can also be correspondingly multiple.

As an example, materials for constructing the flow channel and the droplet orifice 6 include, but are not limited to, silicon, polymers, photoresists, and the like.

Specifically, as shown in FIG. 8, the digital PCR system further includes a pedestal 15, and the PCR reagent chamber 12 is placed in the pedestal 15. As an example, the material of the pedestal 15 includes, but is not limited to, any one of transparent or opaque plastic and glass. The pedestal 15 may be made of metal.

Figure 27:
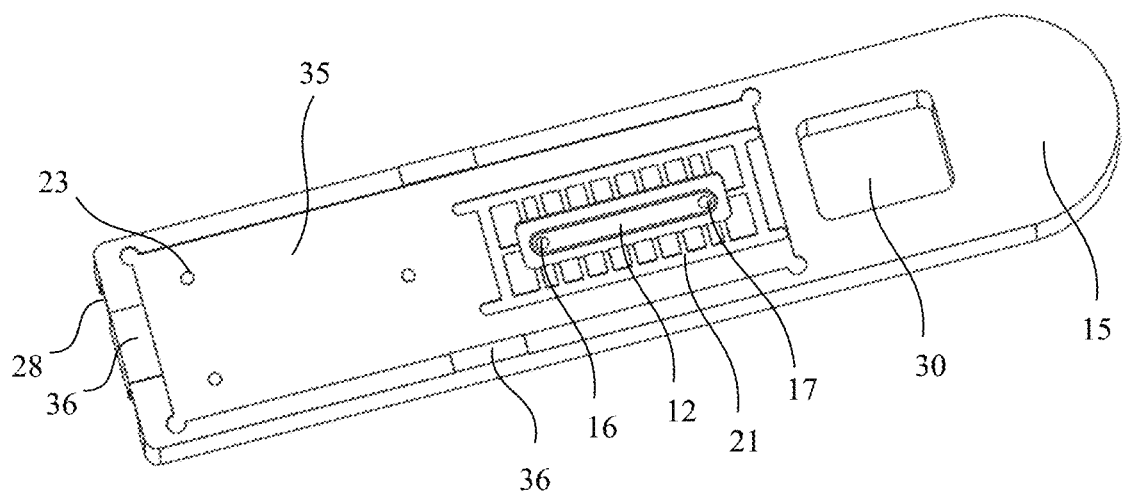
FIG. 27 shows a front view of a pedestal in the digital PCR system of the present disclosure.
Figure 28:
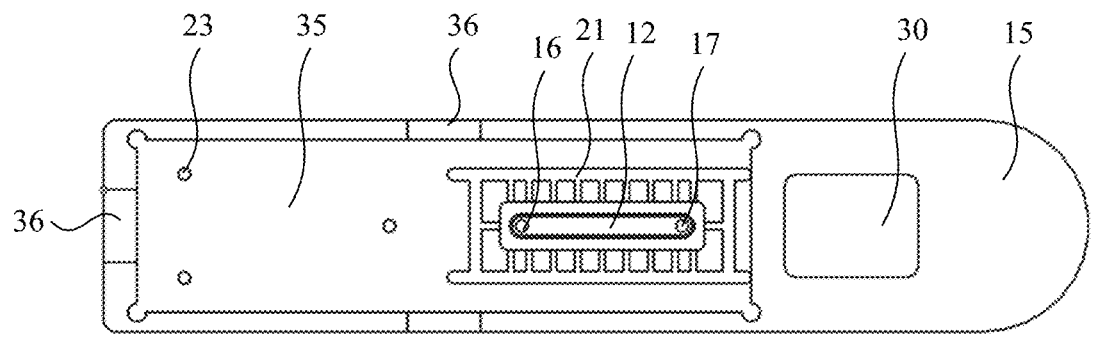
FIG. 28 shows a top view of the pedestal in the digital PCR system of the present disclosure.
Figure 29:
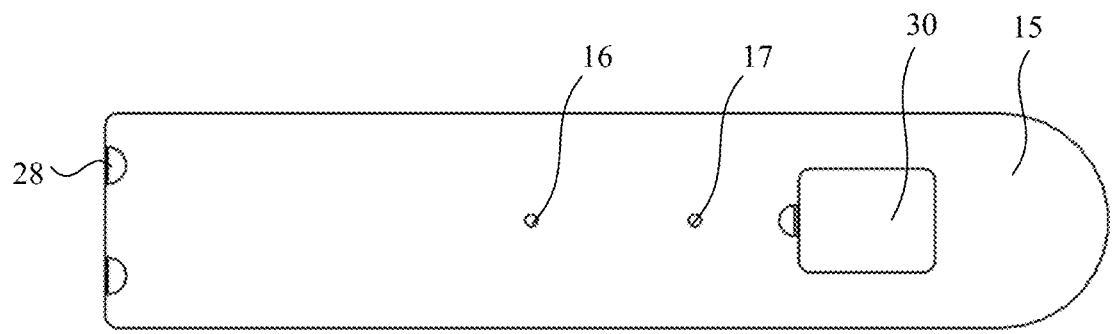
FIG. 29 shows a bottom view of the pedestal in the digital PCR system of the present disclosure.
Figure 30:
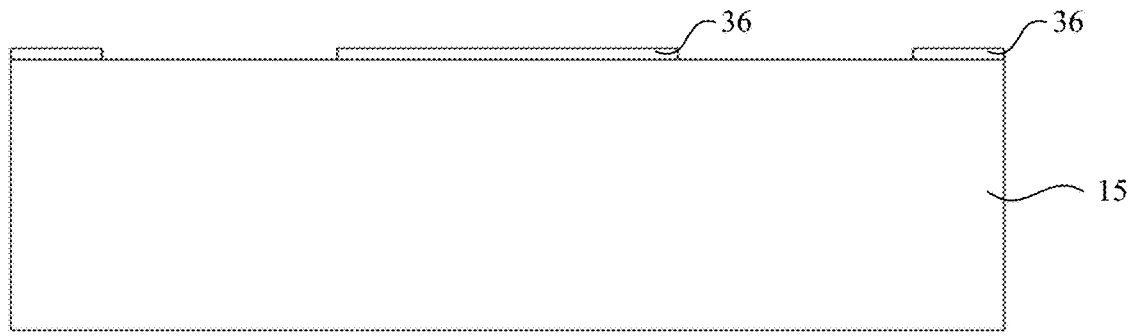
FIGS. 30-33 show side views of the pedestal in the digital PCR system of the present disclosure.
Figure 31:
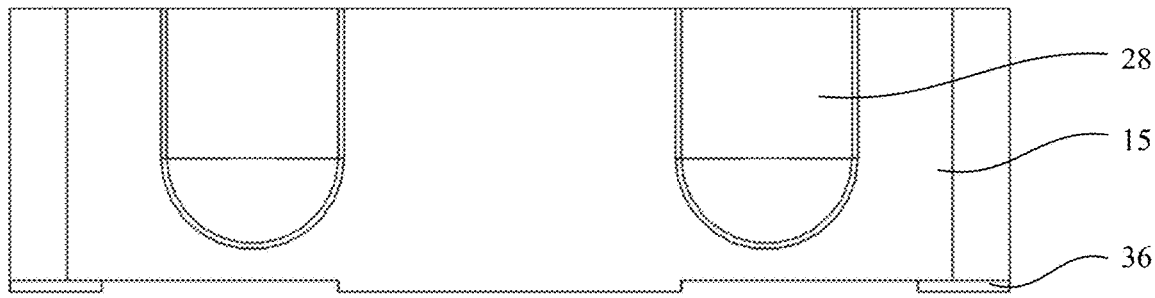
Figure 32:
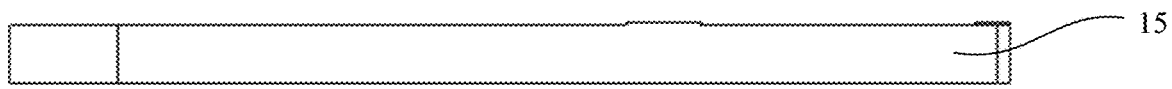
Figure 33:

Referring to FIGS. 27-33. FIG. 27 shows a perspective view of the pedestal. FIG. 28 shows a top view of the pedestal. FIG. 29 shows a bottom view of the pedestal. FIGS. 30-33 show side views of the pedestal in four directions.

Specifically, the PCR reagent chamber 12 contains an opening, the opening extends from the top surface of the pedestal 15 toward the bottom surface of the pedestal 15, but does not penetrate the bottom surface of the pedestal 15, the droplet orifice assembly 5 is coupled with the top surface of the pedestal 15 and covers the opening of the PCR reagent chamber 12.

Specifically, at least one digital PCR solution injection hole 16 is placed on the bottom surface of the pedestal 15, and the digital PCR solution injection hole 16 is connected with the PCR reagent chamber. At least one PCR reagent chamber vent 17 is placed on the bottom surface of the pedestal 15, the PCR reagent chamber vent 17 is connected with the PCR reagent chamber.

Specifically, the flexible circuit board 18 is connected above the pedestal 15. As an example, the flexible circuit board 18 is adhesively attached to the pedestal 15. As shown in FIGS. 27-28, in this embodiment, at least one channel 21 is placed on the surface of the pedestal 15 to prevent glue from flowing onto the droplet orifice assembly 5. The channel 21 is distributed over the outer circumference of the droplet orifice assembly 5.

In this embodiment, a sunken platform 35 is placed on the surface of the pedestal 15 to accommodate the flexible circuit board. The four corners of the sunken platform 35 have a circular arc-shaped extension space. The protrusions 36 around the sunken platform 35 play a role in positioning when the flexible circuit board is adhered to the surface of the sunken platform 35.

As shown in FIG. 19, at least two positioning perforations 22 are placed in the flexible circuit board 18. As shown in FIG. 28, a positioning protrusion protrusions 23 corresponding to a position of the positioning perforation 22 is placed on the surface of the pedestal 15.

Figure 34:
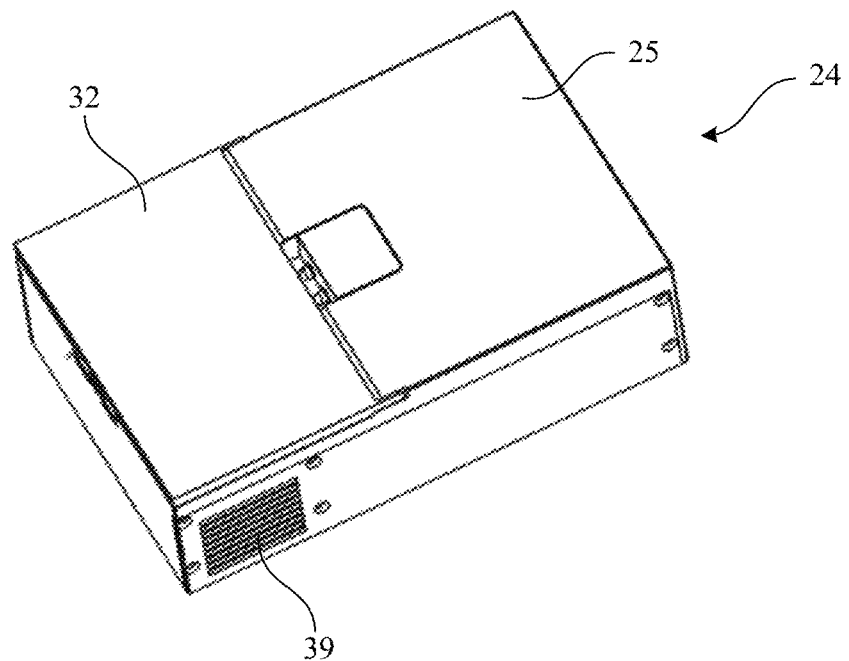
FIG. 34 shows a schematic perspective view of a controller in the digital PCR system of the present disclosure.

Specifically, the digital PCR system further includes a controller 24. Referring to FIG. 34, which is a schematic perspective view of the controller 24. The controller 24 includes a controller housing 25 and a controller circuit board (not shown) located in the controller housing 25. In this embodiment, the controller 24 further includes a cover 32. The cover 32 is coupled with the controller housing 25 to cover the pedestal 15, so as to provide a light-shielding environment for the PCR reaction.

Figure 35:
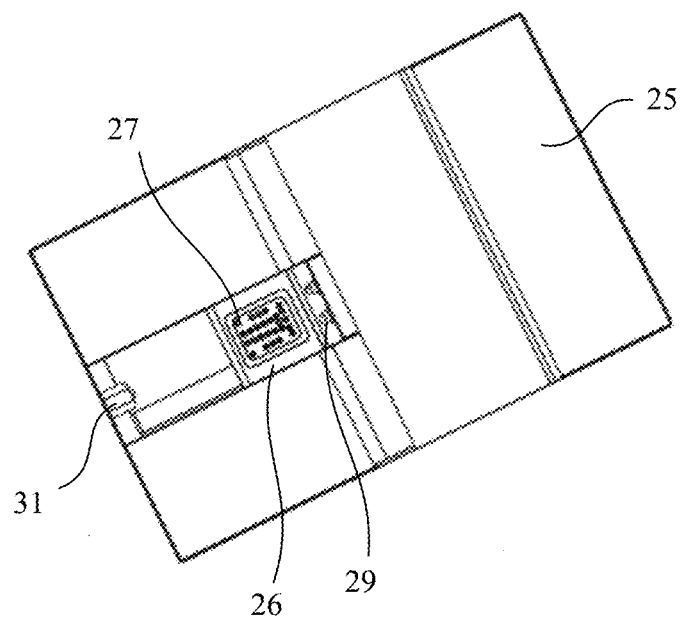
FIG. 35 shows a top view of a controller presented after a cover is removed in the digital PCR system of the present disclosure.

Referring to FIG. 35, which shows a top view of the controller presented after the cover 32 is removed. The controller housing 25 contains a supporting portion 26 to place the pedestal. A plurality of circuit connecting conductive pins 27 electrically connected with the controller circuit board is placed on the surface of the carrying portion 26. The position of the circuit connecting conductive pin 27 corresponds to a position of the second connection pad 20.

Figure 36:
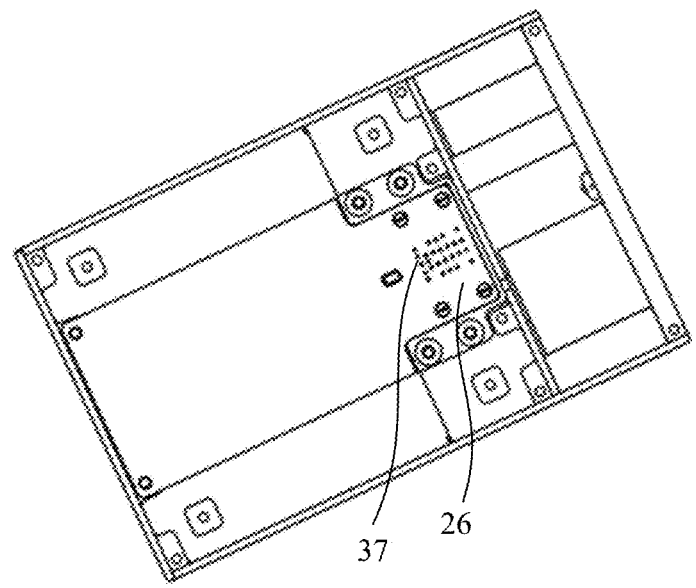
FIG. 36 shows a bottom view of the controller presented after a bottom plate of a controller housing is removed in the digital PCR system of the present disclosure.

Referring to FIG. 36, which shows a bottom view of the controller presented after a bottom plate of a controller housing is removed in the digital PCR system of the present disclosure. A plurality of circuit board connection points 37 corresponding to the circuit connecting conductive pins 27 is placed on the back surface of the supporting portion 26. The controller circuit board may output a signal to the circuit connecting conductive pin 27 through the circuit board connection point 37.

Specifically, as shown in FIG. 27, at least one limiting slot 28 is placed at one end of the pedestal 15. As shown in FIG. 35, at least one limiting member 29 corresponding to the limiting slot 28 is placed at the controller housing 25. The limiting member 29 may be a spring plunger.

Specifically, as shown in FIG. 27, a limiting through hole 30 is placed at the pedestal 15, the limiting through hole 30 penetrates a front surface and a back surface of the pedestal 15. As shown in FIG. 35, a limiting member 31 corresponding to the limiting through hole 30 is placed at the controller housing 25. The limiting member 31 may be a spring plunger.

Specifically, the digital PCR system further includes an external semiconductor cooler to heat or cool the droplet formation chamber, to provide the reaction condition at a particular temperature. The Thermo Electric Cooler (TEC) is made by using the Peltier effect of the semiconductor material. The so-called Peltier effect refers to the phenomenon that when a direct current passes through a galvanic couple composed of two kinds of semiconductor materials, one end of the galvanic couple absorbs heat and the other end radiates heat. The heavily doped N-type and P-type bismuth telluride is mainly used as a semiconductor material of TEC. The bismuth telluride elements are electrically connected in series and are heated in parallel. The TEC includes a number of P-type and N-type pairs (sets) that are joined together by electrodes and sandwiched between two ceramic electrodes. When a current flows past the TEC, the heat generated by the current will pass from one side of the TEC to the other side, resulting in a "hot" side and a "cold" side on the TEC, which is the heating and cooling principle of the TEC.

Figure 37:
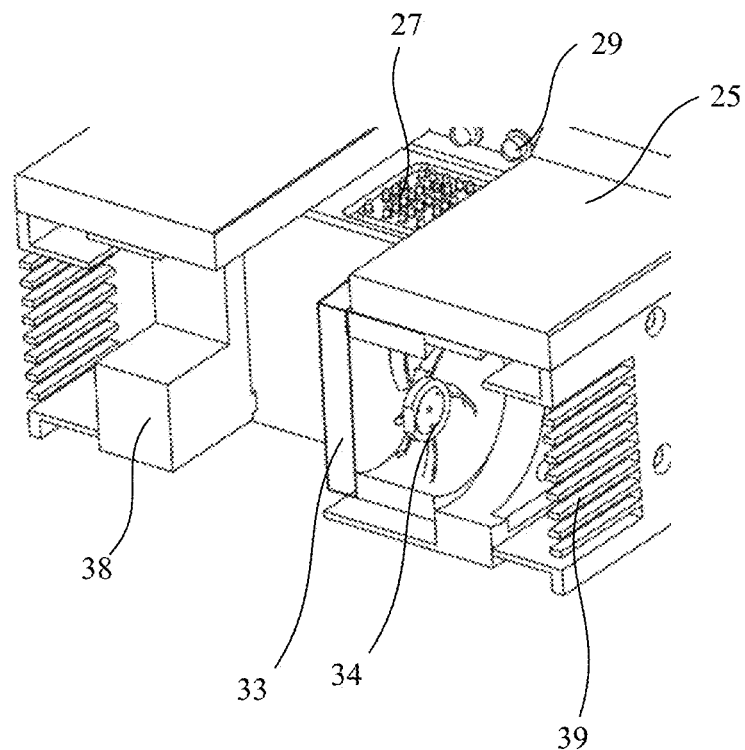
FIG. 37 shows a schematic diagram of an external semiconductor cooler placed in the controller housing in the digital PCR system of the present disclosure.

As an example, referring to FIG. 37, the external semiconductor cooler 33 is placed in the controller housing 25 and located on the side of the heat conducting plate 2 of the droplet formation assembly 1. In this embodiment, the external semiconductor cooler further includes a fan 34. The fan 34 is used to cool the "hot" side when the external semiconductor cooler is cooled, and to heat the "cold" side when the external semiconductor cooler is heated. As shown in FIG. 37, a vent 34 is further placed beside the fan 34. FIG. 37 further shows a housing support structure 16.

Specifically, the digital PCR system further includes an external temperature sensor to test a temperature of the droplet formation chamber. As an example, the external temperature sensor is placed on a surface of the external semiconductor cooler that is in contact with the heat conducting plate.

The digital PCR system further includes an optical detection system to perform PCR signal collection detection without transferring a sample. The optical system mainly includes: a fluorescent light source, a bright field light source, a control circuit, an optically amplified lens set, a fluorescence light filter, a CCD camera, a slide system for moving the lens, and a housing for protecting from light. The photographing area of the optical system is the entire area of the cover plate. This type of shooting may be one shot or multiple shots and stitching pictures.

The digital PCR system of the present disclosure may be used for the formation of digital PCR droplets. The rapid droplet formation depends on the instantaneous vaporization of the nano-thickness liquid layer by the vaporization component in the droplet orifice, thereby rapidly pushing the digital PCR solution in the droplet orifice into the droplet formation oil, to form digital PCR droplets. The droplet formation technique of the present disclosure can achieve a droplet formation speed of greater than 1000 droplets per second, while the formation speed of the system on the market is 100 droplets per second. Compared with the method in which the oil phase and the water phase move together to produce droplets, the oil phase in the technical solution of the present disclosure is static, so the consumption of the oil phase is greatly reduced by about 50%. In-situ temperature-controlled PCR can be achieved by using an external semiconductor cooler to accurately control the temperature of the droplet formation chamber. The integrated optical system can perform test without transferring the sample. This reduces the operating time and improves the accuracy of the detection by reducing human errors. In-situ digital PCR droplets can be tiled.

Embodiment 2

The present disclosure further provides a method for forming digital PCR droplet, including: vaporizing a digital PCR solution through a vaporization component, and rapidly pushing the digital PCR solution into the droplet formation oil in the droplet formation chamber, to form the digital PCR droplet.

As an example, high-speed digital PCR droplet formation is performed by using a thermal bubble technique. The vaporization component includes a heating component that vaporizes the liquid layer of the digital PCR solution by heating.

Specifically, a formation speed of the digital PCR droplet is controlled by controlling a heating time, a number of heating times, and a heating interval time of the heating component. A digital PCR droplet formation rate of greater than 1000 droplets per second can be achieved using the method for forming the digital PCR droplet of the present disclosure.

As an example, the method for forming the digital PCR droplet includes: S1: injecting a digital PCR solution into a PCR reagent chamber, the digital PCR solution enters a droplet orifice communicating with the PCR reagent chamber to form a liquid layer; S2: adding a droplet formation oil to a droplet formation chamber, the droplet formation chamber is formed by a heat conducting plate, a cover plate, and an inverted U-shaped step placed on one side surface of the cover plate; S3: vaporizing the digital PCR solution through a vaporization component, and rapidly pushing the digital PCR solution into the droplet formation oil in the droplet formation chamber, to form the digital PCR droplet.

Specifically, the thickness of the liquid layer is on the order of nanometers and greater than 0.2 nm. In the embodiment, the thickness of the liquid layer is preferably in the range of 0.2 nm to 30,000 nm.

Specifically, a thickness of the droplet formation chamber is less than twice a diameter of the digital PCR droplet to be formed, such that the resulting digital PCR droplet is tiled in the droplet formation chamber.

Specifically, after adding the droplet formation oil to the droplet formation chamber, and before placing the droplet orifice assembly (such as the thermal bubble printing chip) into the controller, a sealing member such as a rubber plug or a sealing film is used to seal the droplet formation oil injection hole placed on the wall of the droplet formation chamber.

Specifically, after the digital PCR solution in the PCR reagent chamber is completely pushed into the droplet formation chamber to form the digital PCR droplet, the PCR reagent chamber is filled with the droplet formation oil, the PCR reagent chamber is in a filled state to prevent the formed droplets from flowing back to the PCR reagent chamber. The droplet formation chamber vent placed on the wall of the droplet formation chamber, the digital PCR solution injection hole placed on the wall of the PCR reagent chamber, and the PCR reagent chamber vent may be sealed by using the sealing member. The sealing member includes, but is not limited to, a rubber plug, a parafilm, an apron ring, a gasket for sealing, and the like. The sealing member can be made of soft plastic such as rubber or PDMS.

Specifically, after the sealing is performed, the droplet formation chamber is heated or cooled by using an external semiconductor cooler, and the droplet formation chamber is controlled at a temperature required for performing PCR to realize in-situ temperature-controlled PCR.

Figure 38:
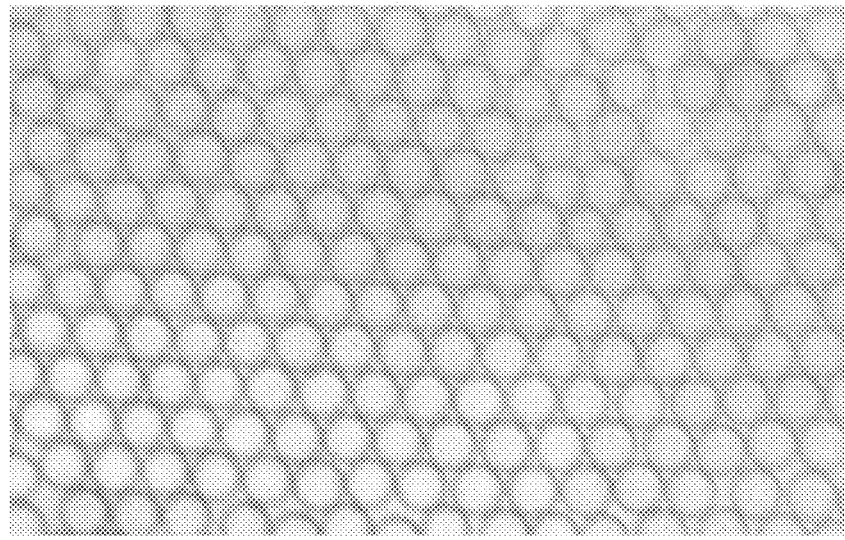
FIG. 38 shows an optical micrograph of digital PCR droplets formed by using the digital PCR system of the present disclosure.
Figure 39:
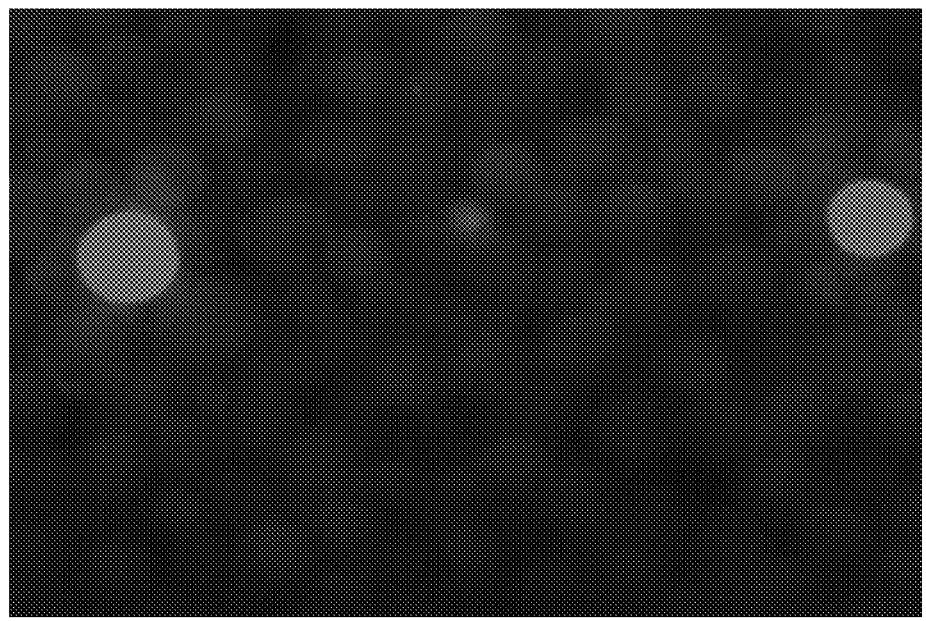
FIG. 39 shows a fluorescence diagram of digital PCR droplets formed by using the digital PCR system of the present disclosure.

Specifically, the integrated optical system can also be used to perform PCR signal collection and detection without transferring the sample. Referring to FIG. 38, which shows an optical micrograph of digital PCR droplets formed by using the digital PCR system of the present disclosure, the formed digital PCR droplets are symmetrical and uniform in morphology.

After the droplets are formed by standard digital PCR, positive droplets with fluorescent signals can be observed after 40 cycles by conventional in-situ PCR temperature-controlled reaction. Referring FIG. 39, which shows a fluorescence diagram of digital PCR droplets formed by using the digital PCR system of the present disclosure.

The digital PCR system and the method for forming the digital PCR droplet of the present disclosure can satisfy the use of all digital PCR biochemical reagents. Many biomarker molecules have very low concentrations in the blood (for example, circulating tumor DNA has only 3 DNA molecules per 2 ml of blood). According to the digital PCR system and the method for forming the digital PCR droplet formation in the present disclosure, the droplet formation number is not limited by the amount of oil used and the speed is high, which make this type of detection possible in digital PCR applications.

In summary, the digital PCR system and the method for forming the digital PCR droplet of the present disclosure use a thermal bubble technique to form high-speed digital PCR droplet. The rapid droplet formation depends on the instantaneous heating and vaporization of the nano-thickness liquid layer by the vaporization component in the droplet orifice, thereby rapidly pushing the digital PCR solution in the droplet orifice into the droplet formation oil, to form digital PCR droplets. The droplet formation technique of the present disclosure can achieve a droplet formation speed of greater than 1000 droplets per second, while the formation speed of the product on the market is 100 droplets per second. Compared with the method in which the oil phase and the water phase move together to produce droplets, the oil phase in the technical solution of the present disclosure is static, so the consumption of the oil phase is greatly reduced, and the amount of oil phase is reduced by about 50%. In-situ temperature-controlled PCR can be achieved by using an external semiconductor cooler to accurately control the temperature of the droplet formation chamber. The integrated optical system can be tested without transferring the sample. This reduces the operating time and improves the accuracy of the detection by reducing human errors. In-situ digital PCR droplets can be tiled. Therefore, the present disclosure effectively overcomes various shortcomings in the prior art and has high industrial utilization value.

The above-mentioned embodiments are just used for exemplarily describing the principle and effects of the present disclosure instead of limiting the present disclosure. Those skilled in the art can make modifications or changes to the above-mentioned embodiments without going against the spirit and the range of the present disclosure. Therefore, all equivalent modifications or changes made by those who have common knowledge in the art without departing from the spirit and technical concept disclosed by the present disclosure shall be still covered by the claims of the present disclosure.

We claim:

1. A digital PCR system, comprising:
   a droplet formation assembly, comprising a heat conducting plate and a cover plate, wherein
      at least one inverted U-shaped step is placed on a side surface of the cover plate, and
      the heat conducting plate, the cover plate and the inverted U-shaped step together form a droplet formation chamber having an opening at a bottom; and
   a droplet orifice assembly connected below the droplet formation assembly, comprising a plurality of droplet orifices, wherein
      the droplet orifice is opened from a top surface of the droplet orifice assembly, and extends toward a bottom surface of the droplet orifice assembly, but does not penetrate the lower surface of the droplet orifice assembly,
      the droplet orifice is connected with the droplet formation chamber, and
      a vaporization component is placed in the droplet orifice, the vaporization component vaporizes a digital PCR solution in the droplet orifice and rapidly pushes the digital PCR solution into a droplet forming oil in the droplet formation chamber, to form a digital PCR droplet.

2. The digital PCR system according to claim 1, wherein the droplet orifice assembly comprises a thermal bubble print chip.

3. The digital PCR system according to claim 1, wherein a height of the inverted U-shaped step is less than twice a diameter of the digital PCR droplet to be formed, such that the digital PCR droplet is tiled in the droplet formation chamber.

4. The digital PCR system according to claim 1, wherein a side surface of the heat conducting plate facing the cover plate contains a boss placed along an outer edge of the inverted U-shaped step.

5. The digital PCR system according to claim 1, wherein a part of the heat conductive plate close to the opening of the droplet formation chamber gradually extends outward to form a slope, so as to expand a size of the opening of the droplet formation chamber.

6. The digital PCR system according to claim 1, wherein the droplet formation assembly further comprises at least one droplet formation oil injection hole, the droplet formation oil injection hole penetrates the heat conducting plate and is connected with the droplet formation chamber.

7. The digital PCR system according to claim 1, wherein the droplet formation assembly further comprises at least one droplet formation chamber vent, the droplet formation chamber vent penetrates the heat conducting plate and is connected with the droplet formation chamber.

8. The digital PCR system according to claim 1, wherein the vaporization component is placed on a bottom surface or a side wall of the droplet orifice.

9. The digital PCR system according to claim 1, wherein a shape of the opening of the droplet orifice comprises any one of a circle, an ellipse, and a polygon.

10. The digital PCR system according to claim 1, wherein the vaporization component comprises a heating component, the heating component vaporizes the liquid layer of the digital PCR solution by heating.

11. The digital PCR system according to claim 10, wherein the heating component comprises at least one metal layer.

12. The digital PCR system according to claim 1, wherein
the PCR system further comprises at least one PCR reagent chamber storing a digital PCR solution,
a flow channel is placed in the droplet orifice assembly, and
the droplet orifice is connected with the PCR reagent chamber through the flow channel.

13. The digital PCR system according to claim 12, wherein the flow channel comprises at least one main flow channel and a plurality of branch flow channels connected with the main flow channel, and each of the droplet orifices is respectively connected with one of the branch flow channels.

14. The digital PCR system according to claim 12, wherein
the digital PCR system further comprises a pedestal,
the PCR reagent chamber contains an opening,
the opening extends from a top surface of the pedestal toward a bottom surface of the pedestal but does not penetrate the bottom surface of the pedestal, and
the droplet orifice assembly is coupled with the top surface of the pedestal and covers the opening of the PCR reagent chamber.

15. The digital PCR system according to claim 14, wherein at least one digital PCR solution injection hole is placed on the bottom surface of the pedestal, and the digital PCR solution injection hole is connected with the PCR reagent chamber.

16. The digital PCR system according to claim 14, wherein at least one PCR reagent chamber vent is placed on the bottom surface of the pedestal, and the PCR reagent chamber vent is connected with the PCR reagent chamber.

17. The digital PCR system according to claim 14, wherein
the digital PCR system further comprises a flexible circuit board,
the flexible circuit board is connected above the pedestal,
a through hole is placed in the flexible circuit board to accommodate the droplet orifice assembly,
a plurality of first connection pads and a plurality of second connection pads are placed on a surface of the flexible circuit board, and
the droplet orifice assembly is connected with the first connection pad by a wire.

18. The digital PCR system according to claim 17, wherein the flexible circuit board is adhesively attached to the pedestal.

19. The digital PCR system according to claim 18, wherein at least one channel is placed on the surface of the pedestal to prevent glue from flowing onto the droplet orifice assembly, the channel is distributed over the outer circumference of the droplet orifice assembly.

20. The digital PCR system according to claim 17, wherein at least two positioning perforations are placed in the flexible circuit board, a positioning protrusion corresponding to a position of the positioning perforation is placed on the surface of the pedestal.

21. The digital PCR system according to claim 14, wherein
the digital PCR system further comprises a controller,
the controller comprises a controller housing and a controller circuit board located in the controller housing,
the controller housing contains a supporting portion to place the pedestal,
a plurality of circuit connecting conductive pins connected with the controller circuit board is placed on a surface of the supporting portion, and
a position of the circuit connecting conductive pin corresponds to a position of the second connection pad.

22. The digital PCR system according to claim 21, wherein at least one limiting slot is placed at one end of the pedestal, and at least one limiting member corresponding to the limiting slot is placed at the controller housing.

23. The digital PCR system according to claim 21, wherein a limiting through hole is placed at the pedestal, the limiting through hole penetrates a front surface and a back surface of the pedestal, and a limiting member corresponding to the limiting through hole is placed at the controller housing.

24. The digital PCR system according to claim 21, wherein the controller further comprises a cover, the cover is coupled with the controller housing to cover the pedestal.

25. The digital PCR system according to claim 1, further comprising: an external semiconductor cooler to heat or cool the droplet formation chamber.

26. The digital PCR system according to claim 25, wherein the external semiconductor cooler contains a fan.

27. The digital PCR system according to claim 25, further comprising: an external temperature sensor to detect a temperature of the droplet formation chamber.

28. The digital PCR system according to claim 1, further comprising: an optical detection system performing PCR signal collection detection without transferring a sample.

29. The digital PCR system according to claim 1, wherein a material of the cover plate is transparent.

30. A method for forming digital PCR droplet, comprising:
injecting a digital PCR solution into a PCR reagent chamber, the digital PCR solution enters a droplet orifice connecting with the PCR reagent chamber to form a liquid layer;
adding a droplet formation oil to a droplet formation chamber, wherein the droplet formation chamber is formed by a heat conducting plate, a cover plate, and an inverted U-shaped step placed on one side surface of the cover plate; and vaporizing the digital PCR solution through a vaporization component, and rapidly pushing the digital PCR solution into the droplet formation oil in the droplet formation chamber to form the digital PCR droplet.

31. The method for forming digital PCR droplet according to claim 30, wherein the vaporization component comprises a heating component that vaporizes the liquid layer by heating.

32. The method for forming digital PCR droplet according to claim 31, wherein a formation speed of the digital PCR droplet is controlled by controlling a heating time, a number of heating times, and a heating interval time of the heating component.

33. The method for forming digital PCR droplet according to claim 30, wherein a thickness of the liquid layer ranges from 0.2 nm to 30,000 nm.

34. The method for forming digital PCR droplet according to claim 30, wherein a thickness of the droplet formation chamber is less than twice a diameter of the digital PCR droplet to be formed, such that the digital PCR droplet is tiled in the droplet formation chamber.

35. The method for forming digital PCR droplet according to claim 30, wherein after the digital PCR solution in the PCR reagent chamber is completely pushed into the droplet formation chamber to form the digital PCR droplet, the PCR reagent chamber is filled with the droplet formation oil.

36. The method for forming digital PCR droplet according to claim 30, wherein the droplet formation chamber is heated or cooled by an external semiconductor cooler.

37. The method for forming digital PCR droplet according to claim 30, wherein the digital PCR droplet is formed at a rate greater than 1000 droplets per second.

* * * * *